(12) United States Patent
Kleefstra

(10) Patent No.: US 6,970,799 B2
(45) Date of Patent: Nov. 29, 2005

(54) METHOD AND APPARATUS FOR PARTICLE SIZING

(75) Inventor: Meindert J. Kleefstra, Vancouver, WA (US)

(73) Assignee: AirAdvice, Inc., Portland, OR (US)

( * ) Notice: Subject to any disclaimer, the term of this patent is extended or adjusted under 35 U.S.C. 154(b) by 0 days.

(21) Appl. No.: 10/678,319

(22) Filed: Oct. 2, 2003

(65) Prior Publication Data

US 2004/0068389 A1 Apr. 8, 2004

Related U.S. Application Data

(60) Provisional application No. 60/415,911, filed on Oct. 2, 2002.

(51) Int. Cl.[7] .......................... G01D 1/00; G01N 31/00; G01N 21/00
(52) U.S. Cl. .......................... 702/128; 702/29; 356/339
(58) Field of Search ..................... 702/29, 128, 155, 702/156, 157; 356/339

(56) References Cited

U.S. PATENT DOCUMENTS

| | | | | |
|---|---|---|---|---|
| 3,882,382 A | | 5/1975 | Coulter et al. | |
| 4,009,443 A | * | 2/1977 | Coulter et al. | 327/26 |
| 4,205,384 A | * | 5/1980 | Merz et al. | 702/29 |
| 4,305,665 A | | 12/1981 | Achter et al. | |
| 4,375,334 A | * | 3/1983 | Gerber | 356/336 |
| 4,488,248 A | * | 12/1984 | Okada et al. | 702/21 |
| 4,547,070 A | | 10/1985 | Moll et al. | |
| 4,889,815 A | * | 12/1989 | Bradwell et al. | 436/517 |
| 5,085,500 A | * | 2/1992 | Blesener | 356/338 |
| 5,286,452 A | * | 2/1994 | Hansen | 422/73 |
| 5,870,190 A | * | 2/1999 | Unger | 356/336 |
| 5,999,250 A | * | 12/1999 | Hairston et al. | 356/73 |
| 6,337,564 B2 | | 1/2002 | Manzini et al. | |

* cited by examiner

Primary Examiner—Bryan Bui
Assistant Examiner—Meagan S Walling
(74) Attorney, Agent, or Firm—Schwabe, Williamson & Wyatt, P.C.

(57) ABSTRACT

A method and apparatus provides for particle size detection. A particle detector signal is utilized to provide particle size information. The particle detection signal is obtained by utilizing particle detector information.

30 Claims, 7 Drawing Sheets

METHOD AND APPARATUS FOR PARTICLE SIZING

RELATED APPLICATION

This application claims priority to U.S. Provisional Application number 60/415,911, titled "Particle Sizing Method", filed on Oct. 2, 2002, which is hereby fully incorporated by reference.

BACKGROUND OF THE INVENTION

1. Field of the Invention

The present invention relates to the field of hygiene. More specifically it relates to the monitoring of airborne contaminants inside structures, including but are not limited commercial, industrial, and residential buildings, as well as public transportation, airplane, train, ship, and the like.

2. Background Information

The measurement of indoor aerosols is a key activity in diagnosing indoor air quality problems in buildings, residences, public offices, manufacturing sites, public transportation and other places where people spend extended time indoors. These aerosols can vary in composition and concentration by location, geography, time-of-day and other factors. Identifying the size distribution of the indoor aerosol is very important in diagnosing and fixing indoor air quality problems. Size is considered a strong function of the origin of the contaminant. For example, cigarette smoke particles are generally less than 1 micron in size where most pollens range from 5–50 microns in size.

Light scattering instruments have been used for the past 20 years to quantify the amount of aerosol by providing a single number that can be used to estimate the total concentration in units of mass/volume, e.g. micrograms per cubic meter. These instruments are typically expensive, heavy, and provide only a simple snapshot of the distribution of particles in an aerosol.

3. Terminology

Throughout the remaining specification, including the claims, usage of the term "particle" is intended to include aerosols found in buildings, residences, mass transportation vehicles etc., such as: general particulate matter, fine dust from building materials, plants and animal allergens, mold and mildew spores, the inflammatory, toxic or mutagenic residue from the growth of mold or gram negative bacteria, man-made pollution such as exhaust from fuel combustion, and any other matter suspended in the ambient air in the form of an aerosol that will scatter light. Further, the use of the term "nephelometer" applies to a general class of instruments that use scattered light measurement to quantity the amount and provide information on the size of particles in an indoor aerosol.

BRIEF DESCRIPTION OF DRAWINGS

Embodiments of the present invention will be described referencing the accompanying drawings in which like references denote similar elements, and in which.

DETAILED DESCRIPTION OF THE PREFERRED EMBODIMENTS

Figure 1:
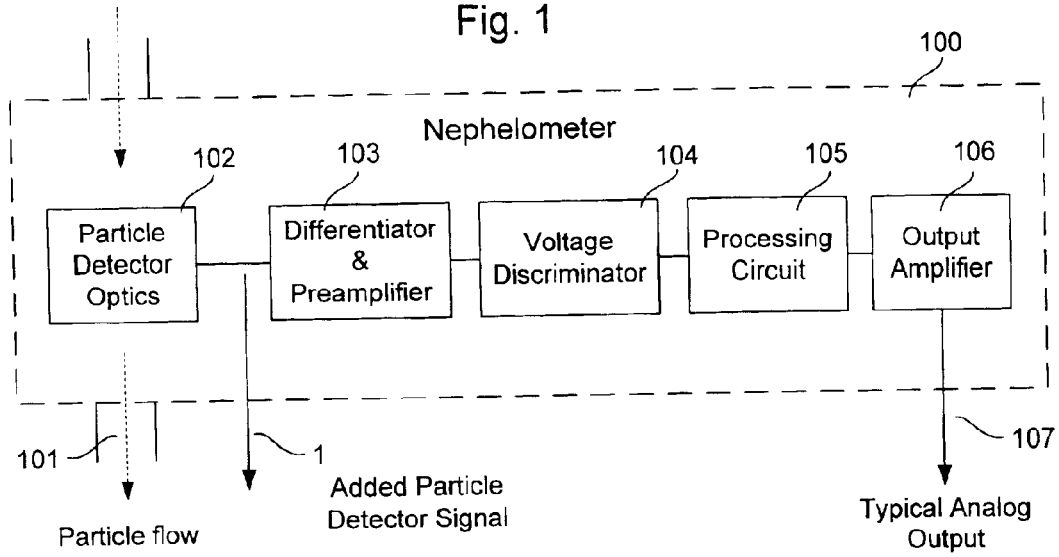
FIG. 1 illustrates the digitization of amplified pulses from the detector of a nephelometer into four channels that are determined by voltage levels on four comparators, in accordance with one embodiment.

Embodiments of particle sizing methodology and apparatus are described herein. In the following description, numerous specific details are set forth to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Overview

The scattered light signal from the light detector of a nephelometer, resulting from a particle moving through the focal point by simple movement of air, can be measured. When the signal is strong enough to be distinguished from background noise, amplified and connected to several signal level discriminators or comparators, the resulting signal can then be processed by various methods. A typical nephelometer has an optical section, a differentiator to select particle related signals from background light and pre-amplifier to enhance the signal level. The resulting signal is fed to a discriminator and a charging circuit that produces an averaged signal and is proportional to mass per volume of air. The invention makes use of the signal prior to the built-in discriminator. During this discussion, the signal prior to the built-in discriminator is referred to as the particle detector signal.

A larger particle results in a larger signal at the particle detector signal, likely triggering a voltage discriminator with a higher voltage reference level. Taking advantage of this, several channels can be designed to represent pulses from particles able to trigger the discriminator for each channel. The data from these channels can then be analyzed to determine the ratio of particles in each channel. This process is independent of the airflow within certain levels as all particles are drawn through the detector at virtually the same speed. Depending on the number of channels, a histogram can be calculated from the data of each channel. This channel information can be obtained by counting the number of pulses of each channel in a preset time interval. Assuming that the lowest particle size range is represented by channel A, the middle particle size range by channel B and the largest particle size range by channel C; the percentages of each channel can be calculated in the following way from the total particle distribution.

Percentage of particles in range $A=(A-B)/A$

Percentage of particles in range $B=(B-C)/A$

Percentage of particles in range $C=C/A$

The typical analog output of the nephelometer provides the total particulate level and is fairly independent of airflow. The analog value is proportional to the total mass per volume of particles in the air. The invention provides the additional particle sizing information for a nephelometer. The particle sizing results are fairly independent of airflow since the particle sizing information is ratio metric as expressed by the equation above. When the airflow changes, all of the particle size ranges are affected by the same relative change. For applications where the airflow is well defined, a more accurate particle count per volume of air can be measured.

The invention also provides a means to add particle size dependent analog output channels that provide data is expressed as mass per volume of air for particles larger than set by the added discriminator.

The output formats of the invention include (A) relative pulse data per particle size, (B) calculated mass per volume of air for each particle size range and/or (C) direct analog output in mass per volume of air similar to the traditional output of the nephelometer.

While a typical nephelometer expresses particles in the air in mass per volume of air, a particle counter will yield particles per volume of air. The invention adds (A) absolute and ratio metric particle size information and (B) particle size count to a typical nephelometer by extracting the analog signal from the preamplifier output.

DETAILED DESCRIPTION

The scattered light signal from the light detector of a nephelometer resulting from a particle moving through the focal point by simple movement of air can be measured by converting the light signal to an electrical signal that can be connected to particle detector signal to obtain specific size data of that particle. An example of a nephelometer 100 is illustrated in FIG. 1. The device has the ability to separate particle signals from background light. A particle 101 passes the particle detector optics 102 that detect its scattered light. The electrical signal from detector 102 is separated from background light and amplified by differentiator amplifier 103. The resulting analog pulse is connected to a voltage discriminator to separate particle signals from noise signals. A discriminator is a device to provide an output when an input is over a given voltage or trigger level. This device is also known as voltage comparator. Processing circuit 105 and output amplifier 106 typically provide an analog voltage proportional with mass per volume of air. However, the added particle detector signal 1, at the output of particle detector 102, can be used to obtain particle-sizing information.

Figure 2:
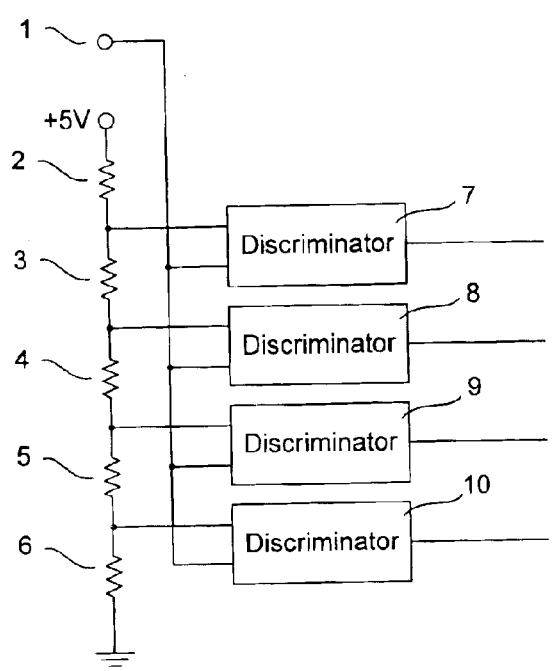
FIG. 2 illustrates comparing a particle detector signal to different trigger levels of different discriminators, in accordance with one embodiment.
Figure 4:
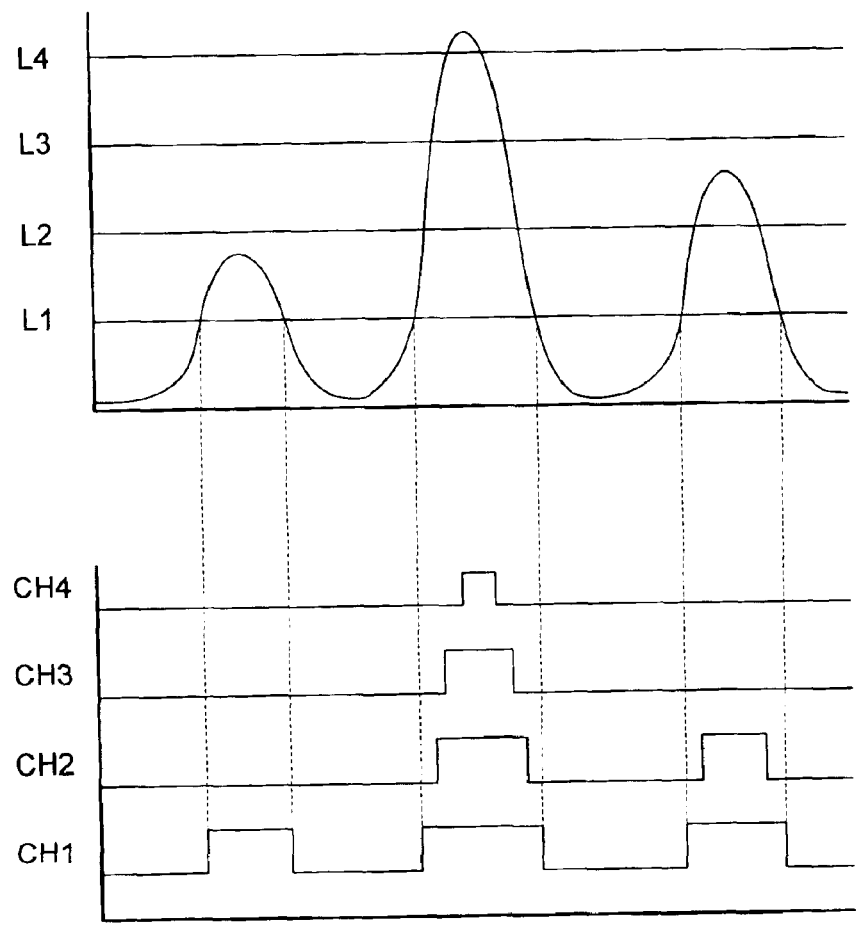
FIG. 4 illustrates the signal representing the amplified pulses from the detector of a nephelometer and conversion to digital pulses via comparators, in accordance with one embodiment.

As illustrated in FIG. 2, the added particle detector signal 1 can be compared to four trigger levels of discriminators 7, 8, 9 and 10, in accordance with one embodiment. The trigger levels are set by resistors 2, 3, 4, 5 and 6. Discriminator 10 has a lowest trigger level and discriminator 7 has a highest trigger level. The resulting digital pulses from such an analog signal are depicted in FIG. 4; higher pulses represent larger particles. Channels CH1–4 show pulses of particles that are equal to or larger than the certain particle sizes. All pulses of a minimal particle detection size trigger, L1, are represented in channel CH1. Each subsequent channel represents particles higher than its correspondingly assigned trigger level L1–L4. FIG. 4 also shows when particle detector signal pulses, from different particle sizes resulting in different amplitudes, trigger various levels of four discriminators with levels L1, L2, L3 and L4. A small particle will yield only a small signal and result in a single pulse in channel CH1, while a larger particle may exceed the trigger levels of discriminators with higher trigger levels and yield a pulse.

Figure 5:
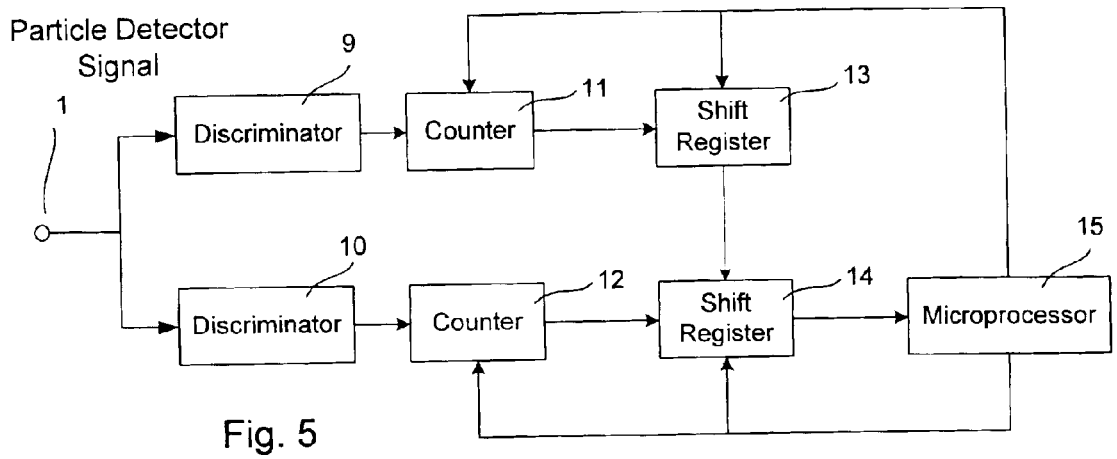
FIG. 5 illustrates the arrangement reading the information of e.g. two channels and transferring it to a microcontroller, in accordance with one embodiment.

The particle size distribution can be obtained in several ways. The embodiment of FIG. 5 shows two channels. The analog particle detector signal 1 is connected to discriminators 9 and 10. Discriminator 9 is connected to a counter device 11. The parallel output bus of counter 11 is connected to a parallel to serial shift register 13. Discriminator 10 is connected to counter 12. The parallel output bus of counter 12 is connected to a parallel to shift register 14. The serial output of shift register 13 is fed to shift register 14. The output of shift register 14 is also connected to microprocessor 15. The microprocessor 15 also controls the timing of the counters and shift registers. In one embodiment, the execution could be as follows. Microprocessor 15 enables counters 11 and 12 for a fixed time period, then clocks the data into shift registers 13 and 14 and finally resets counters 11 and 12 for the next time period and clocks the data into the microprocessor 15 for further processing. The channel pulse distribution can be calculated from the ratio metric data from the channels. In alternative embodiments, other processing devices such as microcontrollers and digital signal processor may be utilized to perform the functions of, at least, the microprocessor.

Figure 6:
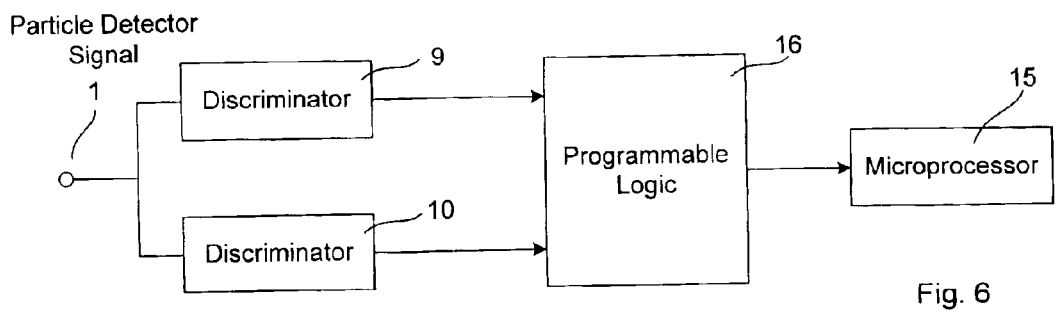
FIG. 6 illustrates a similar arrangement as in FIG. 5, but implemented in programmable logic or ASIC, in accordance with one embodiment.
Figure 7:
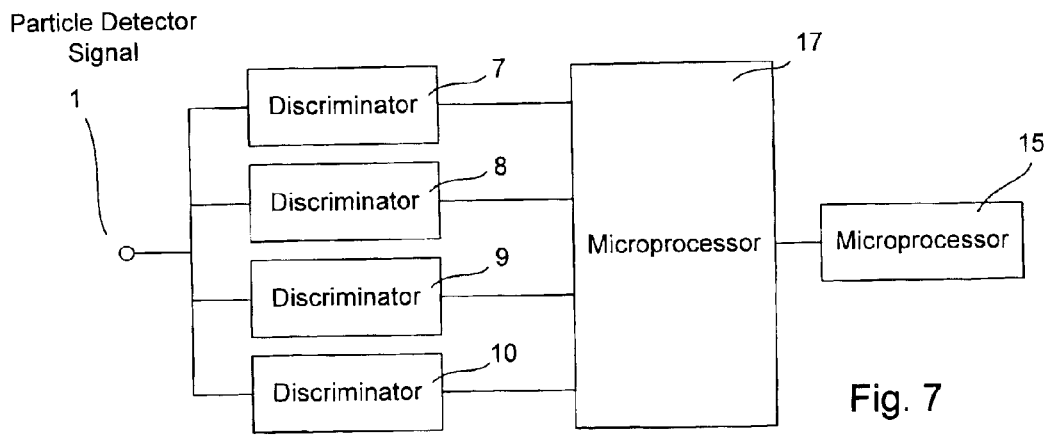
FIG. 7 illustrates the implementation of four channels using a dedicated microcontroller, in accordance with one embodiment.

FIG. 6 is a similar embodiment of FIG. 5, but instead of individual counters and shift registers, programmable logic 16 such as a PLD or an ASIC is used. This may be a more economical implementation in case more than two channels are needed. The output of programmable logic 16 is connected to microprocessor 15. Further reduction is possible, as shown in FIG. 7, by using a dedicated microprocessor 17 to analyze the data in the channels directly and transfer the results to the main system microprocessor 15. If microprocessor 15 has enough I/O pins, then microprocessor 17 can be eliminated also.

Figure 8:
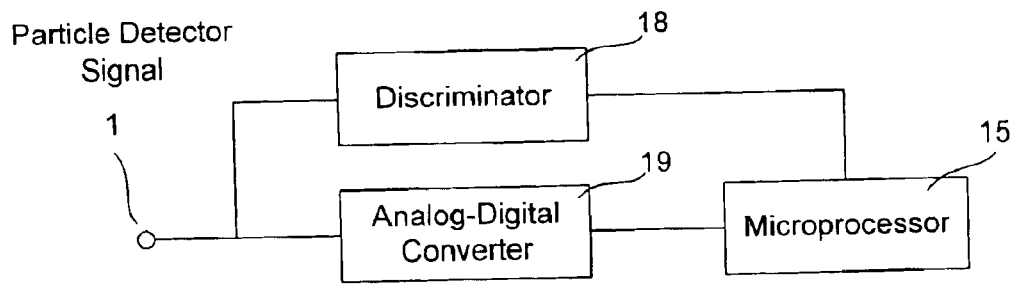
FIG. 8 illustrates the direct reading of the analog data from FIG. 1 with an Analog to Digital converter, accordance with one embodiment.
Figure 9:
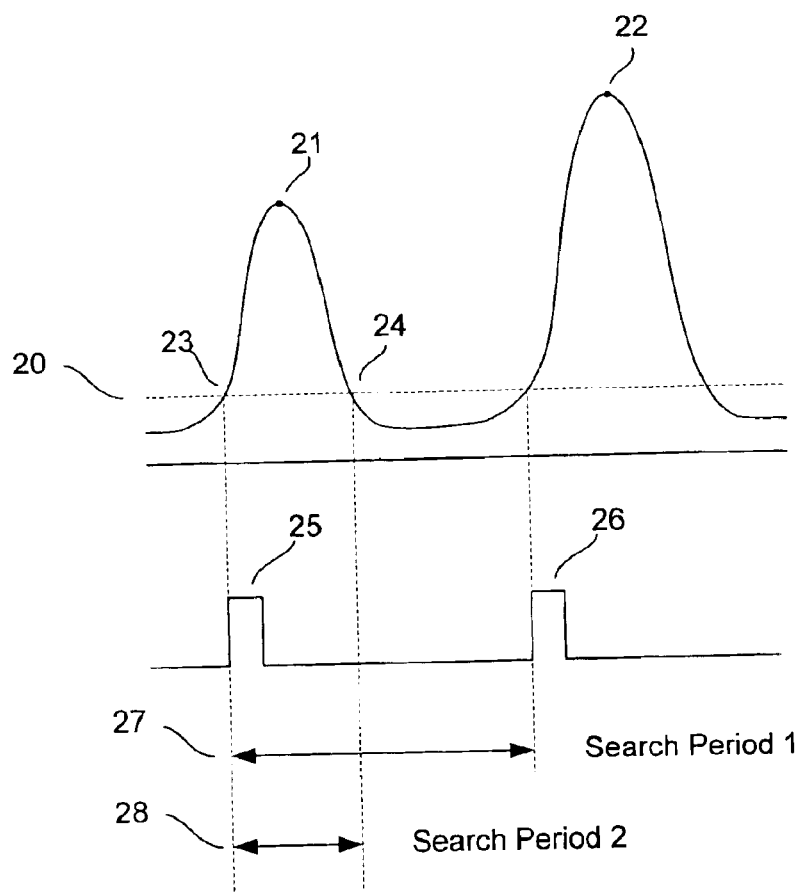
FIG. 9 illustrates an exemplary method of analyzing the particle data, accordance with one embodiment.

The particle detector output of the nephelometer can be measured directly with an analog to digital converter. The signal can be digitized and the result categorized to provide a histogram of the particle size distribution. One can measure each particle size by detecting the peak of each analog signal representing the scattered light of a particle. FIG. 8 shows that the particle detector signal 1 can be connected to Analog to Digital (ADC) converter 19. The output of the ADC can be directly connected to the system microprocessor 15. Particle detector signal 1 is also connected to discriminator 18. ADC 19 can continuously take readings according to FIG. 9. ADC 19 provides digitized values to the system microprocessor 15 of the analog particle detector signal illustrated in the top of FIG. 9. The example illustrated in FIG. 9 shows two pulses of different peak values 21 and 22. Trigger level 20 starts search period 28 at time 23 when the input signal exceeds trigger level 20 of discriminator 18. The process is finished after the signal drops below and later exceeds the trigger level 20 again. The period between timestamps 25 and 26 is marked in FIG. 7 as "search period 1" 27. It is also possible to complete the sequence when the signal drops below the trigger level at 24. This results in "search period 2" 28. The peak value is the highest reading during the search period. In another embodiment, it is possible to use a more extensive algorithm without the use of discriminator 18 that continuously searches for peak data.

Figure 10:
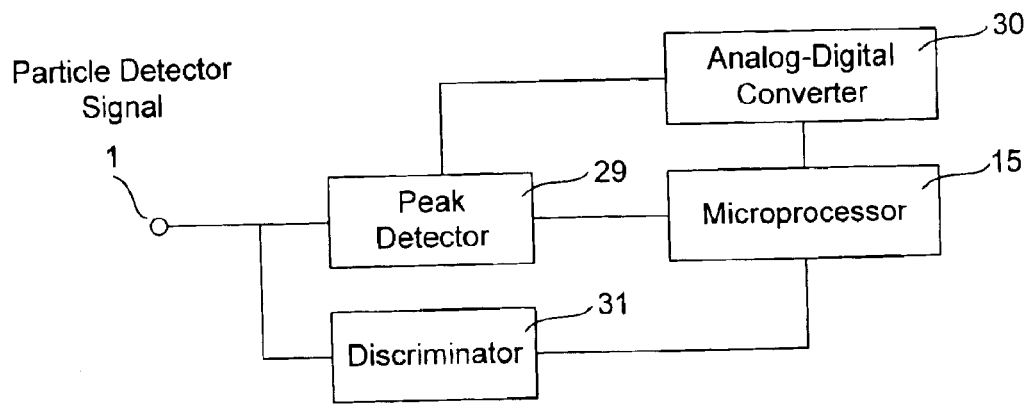
FIG. 10 illustrates analyzing particle data with an Analog to Digital converter and Peak Detector, in accordance with one embodiment.
Figure 11:
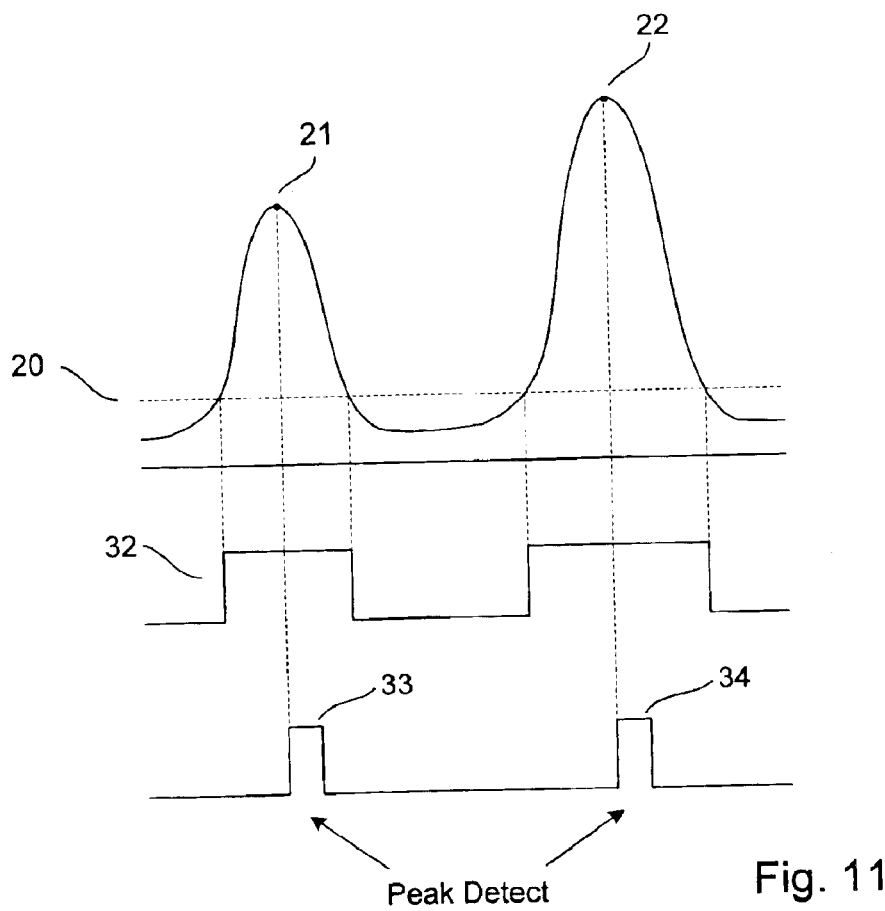
FIG. 11 illustrates the timing sequence of the implementation of FIG. 8, accordance with one embodiment.

A far less calculation intensive solution is in FIG. 10, where peak detector 29 monitors particle detector signal 1 from the nephelometer. Microprocessor 15 monitors discriminator 31 and peak detector 29. Peak detector 29 is enabled when trigger level 20 of FIG. 11 is exceeded. Peak detector 29 is activated when the particle detector signal 1 exceeds trigger level 20 as indicated by pulses 32 generated by discriminator 31. When peak 21 is detected, resulting pulses 33 and 34 capture the peak voltage on sample and hold 61 and start Analog to Digital converter 30 to take a peak reading. The results are read by microprocessor 15. Microprocessor 15 also controls Analog to Digital converter 30. In another embodiment, Analog to Digital converter 30 can be connected to the output of peak detector 29 and sample and hold 61 that also captures and stores the peak value of the pulse. After processing the Analog to Digital converter 30 data, microprocessor 15 resets peak detector 29 for the next event.

Figure 12:
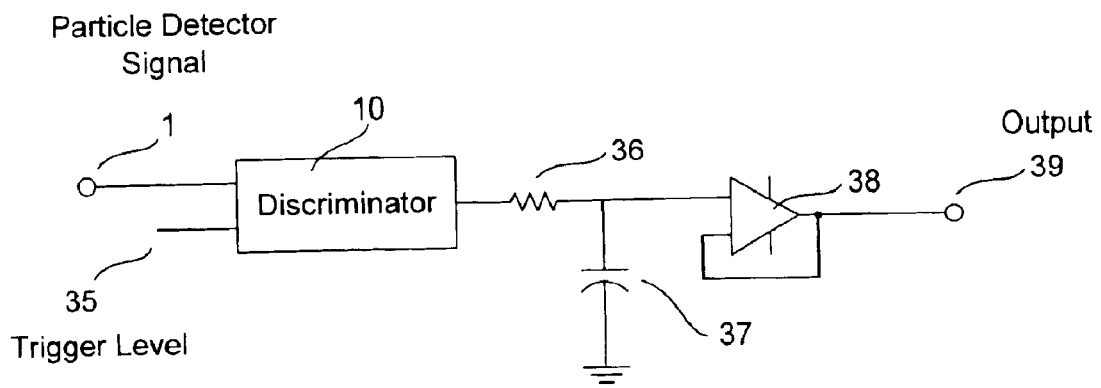
FIG. 12 illustrates an example of the digitization of amplified pulses from the detector of a nephelometer into a channel that is determined by a voltage level on a comparator to provide output data expressed as mass per volume of air, in accordance with one embodiment.

An implementation that does not require a microprocessor is shown in FIG. 12. The particle detector signal 1 is connected to discriminator 10 with trigger level 35. Discriminator 10 output is at zero level when it is not triggered. When a pulse exceeds trigger level 35 then the output is high, e.g. +5V. The output is connected to capacitor 37 via resistor 36. When the output is high, capacitor 37 will be charged by discriminator 10 via resistor 36, otherwise it will be discharged via resistor 36. Low pass filter network resistor 36 and capacitor 37 integrate the pulses produced by discriminator 10 over time. Depending on component selection, the current charging via resistor 36 resembles a current source when operating at relative low voltages. Scaling amplifier 38 is used to produce an analog output voltage on output 39 proportional with mass per volume of air.

Figure 13:
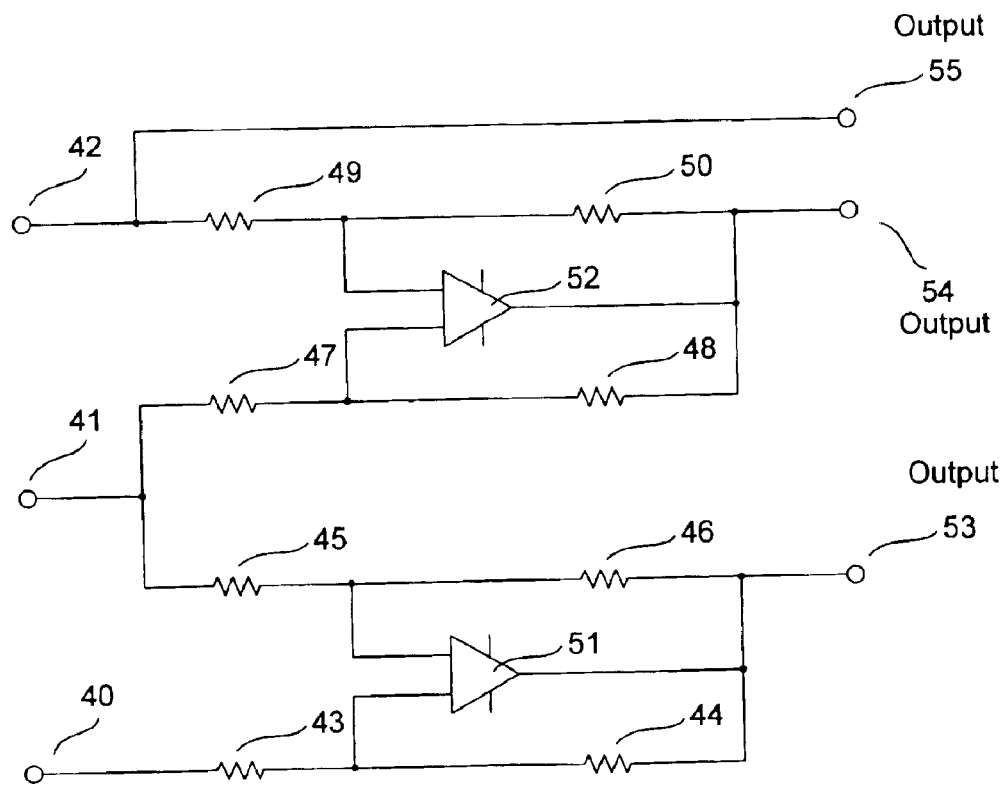
FIG. 13 illustrates an example of analog output data expressed as mass per volume of air for three particle ranges, in accordance with one embodiment.

FIG. 13 shows the additional analog circuitry to create output channels that produce an analog voltage proportional with mass per volume of air for three channels. Input signals 40, 41 and 32 are connected to the output of three circuits as in FIG. 12, each having a different trigger level. The circuit connected to input 40 has a trigger level slightly above the noise level, while 41 and 42 respond to higher trigger levels to accommodate larger particles. Amplifier 51, resistors 43, 44, 45 and 46 serve as a differential amplifier to produce analog output values for particles in the range between 40 and 41. Amplifier 53, resistors 47, 48, 49 and 50 serve as a differential amplifier to produce analog output values for particles in the range between 41 and 42. As a result, output 53 provides an analog output for the smallest particles, while output 54 provides an analog output for medium sized particles and output 55 only responds to larger particles.

The embodiments described in FIG. 1 through FIG. 9 can be used to enhance a particle sensor such as a nephelometer with additional particle details. A 'virtual' particle-sizing sensor can be computed by multiplying the channel count ratios described in the overview above with the traditional analog output of the nephelometer that represents an analog voltage proportional with mass per volume of air. As a result, each calculated value will then represent a value proportional with mass per volume of air for the specific particle sizing range, e.g. 1–2 µm and 2–5 µm. These embodiments require a microprocessor. With the added circuitry of FIG. 12 and FIG. 13, the desired result is obtained without microprocessor computations, and implemented in hardware directly.

Figure 14:
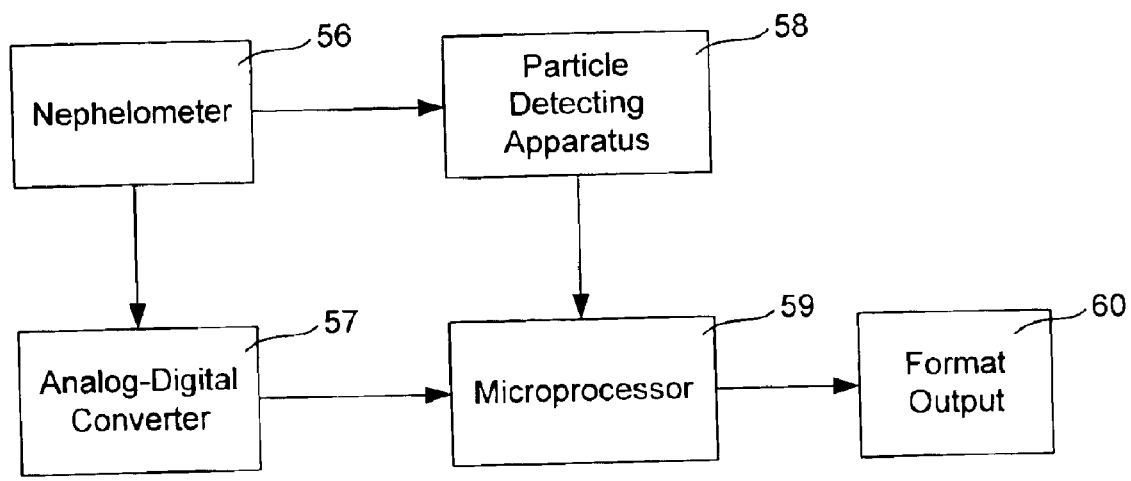
FIG. 14 illustrates an example of providing data expressed as mass per volume of air measured multiple particle size ranges, accordance with one embodiment.

FIG. 14 shows nephelometer 56 and a particle sizing embodiment 58 such as described but not limited to FIGS. 1–9. Analog to Digital converter 57 reads the nephelometer data expressed as mass per volume of air and transfers it to microprocessor 59. Microprocessor 59 also multiplies this data with the ratios of particle sizing embodiment 58 and calculates the output data 60 representing mass per volume of air data for each particle range.

Figure 3:
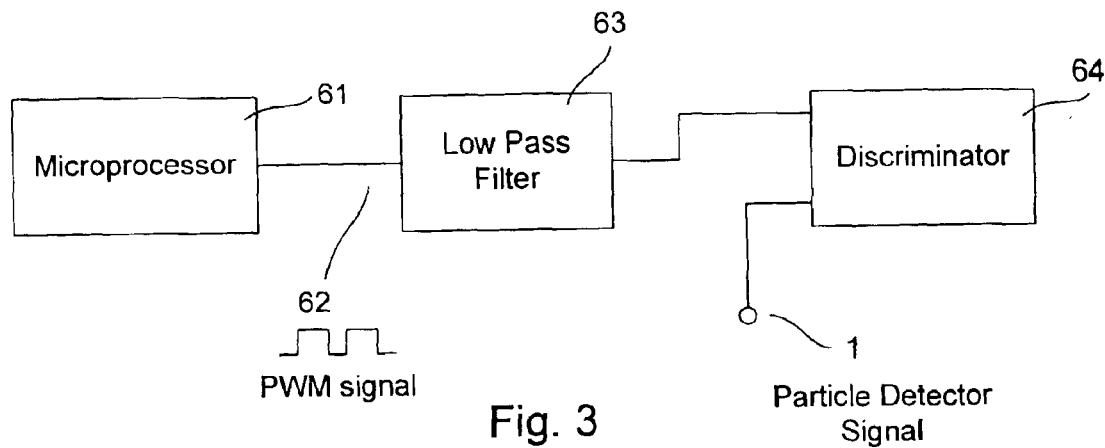
FIG. 3 illustrates programming a threshold level by a microprocessor, in accordance with one embodiment.

The threshold level for a discriminator can be determined by a fixed resistor ratio as in FIG. 1, or may be programmed by a microprocessor such as FIG. 3. Microprocessor 61 generates a Pulse Width Modulated signal 62 that is connected to discriminator 64 via low pass filter 63. The particle detector signal 1 is connected to the other input of discriminator 64. By changing the duty cycle of Pulse Width Modulated 62 signal, the averaged DC level of low pass filter 63 output effectively changes the desired particle size. While FIG. 3 shows one method to provide a means for programmable particle sizing, there are many other embodiments that can accomplish the same, e.g. a microprocessor with built-in Digital to Analog converter. FIG. 3 is only used to describe the basic idea.

Epilogue

Various embodiments for methods and apparatus of detecting particle size distribution are described. In one embodiment, a histogram describes the distribution of particles. This may be an additional piece of data of the analog output of an existing nephelometer representing the total particle level of an air sample. These methods will provide more specific information of the air sample.

As can be seen from the above description, a novel method and apparatus for determining particle sizing is disclosed. The above description of illustrated embodiments of the invention is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize. These modifications can be made to the invention in light of the above description.

What is claimed is:

1. A particle sizing method comprising:
   receiving a measurement value from a nephelometer;
   comparing said received measurement value against a plurality of reference values, said plurality of reference values each indicating a size of a particle;
   providing a particle size of a particle associated with said received measurement value based at least upon said comparing;
   wherein said measurement value is provided by a particle detector of said nephelometer; and
   incrementing a count associated with said particle size upon said providing a particle size.

2. The particle sizing method of claim 1 wherein said measurement value comprises an analog measurement value.

3. A particle sizing apparatus comprising:
   a nephelometer;
   an input coupled to an output of a nephelometer to receive an indicia of particle size wherein said output of said nephelometer is coupled to particle detector of said nephelometer;
   a plurality of discriminators coupled to said input; and
   a reference circuit coupled to said plurality of discriminators, said reference circuit to provide particle size reference information.

4. The particle sizing apparatus of claim 3 wherein said reference circuit comprises a plurality of resistors serially connected between a first reference voltage and a second reference voltage.

5. The particle sizing apparatus of claim 3 further comprising one or more logic devices coupled to said plurality of discriminators, said one or more logic devices to receive data from said plurality of discriminators.

6. The particle sizing apparatus of claim 5 wherein said one or more logic devices comprises a plurality of counters correspondingly coupled to said plurality of discriminators.

7. A particle sizing apparatus comprising:
   an input to receive an indicia of particle size;
   a plurality of discriminators coupled to said input;
   a reference circuit coupled to said plurality of discriminators, said reference circuit to provide particle size reference information;
   one or more logic devices coupled to said plurality of discriminators, said one or more logic devices to receive data from said plurality of discriminators;
   wherein said one or more logic devices comprises a plurality of counters correspondingly coupled to said plurality of discriminators and said one or more logic devices further comprises a plurality of shift registers correspondingly coupled to said plurality of counters.

8. The particle sizing apparatus of claim 7 wherein said one or more logic devices further comprises at least one processing device, selected from the group consisting of a microprocessor, a digital signal processor and a microcontroller and wherein said plurality of shift registers are coupled together and wherein said plurality of shift registers are coupled to said at least one processing device.

9. The particle sizing apparatus of claim 8 wherein said at least one processing device is to analyze pulse data from said discriminators, said pulse data indicating particle size information.

10. A particle sizing apparatus comprising:
    an input to receive an indicia of particle size;
    a plurality of discriminators coupled to said input;
    a reference circuit coupled to said plurality of discriminators, said reference circuit to provide particle size reference information;
    one or more logic devices coupled to said plurality of discriminators, said one or more logic devices to receive data from said plurality of discriminators,
    wherein said one or more logic devices comprises at least one programmable device selected from the group consisting of a Programmable Logic Device (PLD), an Application Specific Integrated Circuit (ASIC), and an Application Specific Standard Product (ASSP).

11. The particle sizing apparatus of claim 10 wherein said one or more logic devices further comprises at least one processing device, selected from the group consisting of a microprocessor, a digital signal processor and a microcontroller, coupled to said at least one programmable device, said at least one processing device to analyze pulse data from said discriminators, said pulse data indicating particle size information.

12. A particle sizing apparatus comprising:
    an input to receive an indicia of particle size;
    a plurality of discriminators coupled to said input;
    a reference circuit coupled to said plurality of discriminators, said reference circuit to provide particle size reference information;
    one or more logic devices coupled to said plurality of discriminators, said one or more logic devices to receive data from said plurality of discriminators,
    wherein said one or more logic devices comprises at least one processing device, selected from the group consisting of a microprocessor, a digital signal processor and a microcontroller, to analyze pulse data from said discriminators, said pulse data indicating particle size information.

13. A particle sizing apparatus comprising:
    an input to receive an indicia of particle size;
    a plurality of discriminators coupled to said input;
    a reference circuit coupled to said plurality of discriminators, said reference circuit to provide particle size reference information;
    a plurality of resistors correspondingly coupled to outputs of said plurality of discriminators; and
    a plurality of capacitors coupled to said plurality of resisters.

14. The particle sizing apparatus claim 13 further comprising one or more scaling amplifiers correspondingly coupled to one or more of said plurality of capacitors.

15. The particle sizing apparatus of claim 14 wherein outputs from said one or more scaling amplifiers provide a voltage proportional with a mass per volume of air.

16. A particle sizing apparatus comprising:
    an input to receive an indicia of particle size;
    a plurality of discriminators coupled to said input;
    a reference circuit coupled to said plurality of discriminators, said reference circuit to provide particle size reference information;
    a plurality of resistors coupled to outputs of said plurality of discriminators; and
    one or more differential amplifiers coupled to said plurality or resistors.

17. The particle sizing apparatus of claim 16 wherein outputs of said differential amplifiers provide analog voltage indications of mass per volume of air for a particle size range.

18. A particle sizing apparatus comprising:
    a plurality of low pass filter circuits;
    a plurality of discriminators correspondingly coupled to said plurality of low pass filter circuits;

a microprocessor coupled to said plurality of low pass filter circuits, said microprocessor to facilitate provision of reference particle size information to said plurality of discriminators; and an input coupled to said plurality of discriminators to receive an indicia of particle size.

19. The particle sizing apparatus of claim 18 wherein said provision of reference particle size information is provided via a pulse width modulated signal.

20. A particle sizing apparatus comprising:

an input to receive an indicia of particle size wherein said input receives an analog indicia of particle size;

an analog to digital converter coupled to said input, said analog to digital converter to provide digital particle size data corresponding to said analog indicia of particle size and to provide peak value indications of said analog indicia of particle size; and at least one processing device, selected from the group consisting of a microprocessor, a digital signal processor and a microcontroller, coupled to said analog to digital converter.

21. The particle sizing apparatus of claim 20 wherein said input to receive an indicia of particle size is coupled to an output of a nephelometer.

22. The particle sizing apparatus of claim 21 wherein said output of said nephelometer is coupled to particle detector of said nephelometer.

23. The particle sizing apparatus of claim 20 further comprising a discriminator coupled to said input and said at least one processing device.

24. The particle sizing apparatus of claim 23 wherein said at least one processing device receives a trigger indicia from said discriminator and analyzes pulse data from said analog to digital converter based at least in part upon said received trigger indicia.

25. A particle sizing apparatus comprising:

an imput to receive an analog indicia of particle size;

a peak detector coupled to said input;

sample and hold circuitry coupled to said peak detector;

an analog to digital converter coupled to said sample and hold circuitry;

at least one processing device, selected from the group consisting of a microprocessor, a digital signal processor and a microcontroller, coupled to said peak detector and said analog to digital converter; and said at least one processing device to receive a trigger indicia from said peak detector and to analyze pulse data from said analog to digital converter based at least in part upon said received trigger indicia.

26. A particle sizing apparatus comprising:

an input to receive an analog indicia of particle size;

a peak detector coupled to said input;

sample and hold circuitry coupled to said peak detector;

an analog to digital converter coupled to said sample and hold circuitry; and at least one processing device, selected from the group consisting of a microprocessor, a digital signal processor and a microcontroller, coupled to said peak detector and said analog to digital converter; and a discriminator coupled to said input and said at least one processing device.

27. The particle sizing apparatus of claim 26 said at least one processing device receives a trigger indicia from at least one of said discriminator and said peak detector and wherein said at least one processing device analyzes pulse data from said analog to digital converter based at least in part upon said received trigger indicia.

28. An apparatus comprising:

particle detector to detect particle related information;

first output circuitry coupled to said particle detector to provide a first output of detected particle related information;

integration circuitry coupled to said particle detector to integrate said particle related information over a period; and second output circuitry coupled to said integration circuitry to provide an average DC analog output related to integrated particle related information.

29. The apparatus of claim 28 wherein said first output is an analog output.

30. The apparatus of claim 28 wherein said particle related information comprises particle size information.

* * * * *

UNITED STATES PATENT AND TRADEMARK OFFICE
CERTIFICATE OF CORRECTION

PATENT NO. : 6,970,799 B2
APPLICATION NO. : 10/678319
DATED : November 29, 2005
INVENTOR(S) : Meindert J. Kleefstra It is certified that error appears in the above-identified patent and that said Letters Patent is hereby corrected as shown below:

In the Claims:

Col. 8, line 43, "...apparatus claim 13..." should read --...apparatus of claim 13...--;

Col. 9, line 38, "...an imput..." should read --...an input...--.

Signed and Sealed this

Twentieth Day of February, 2007

JON W. DUDAS
*Director of the United States Patent and Trademark Office*